US008664161B2

(12) United States Patent　　(10) Patent No.: US 8,664,161 B2
Tandler　　(45) Date of Patent: Mar. 4, 2014

(54) METHOD FOR INCREASING LONG-TERM STORAGE OF CUT FLOWERS

(75) Inventor: Jaron Tandler, Carmei Yosef (IL)

(73) Assignee: Greenoy Ltd., Mobile Post Arava (IL)

( * ) Notice: Subject to any disclaimer, the term of this patent is extended or adjusted under 35 U.S.C. 154(b) by 1398 days.

(21) Appl. No.: 12/263,027

(22) Filed: Oct. 31, 2008

(65) Prior Publication Data

US 2009/0092740 A1　Apr. 9, 2009

Related U.S. Application Data

(63) Continuation-in-part of application No. PCT/IL2007/000529, filed on May 1, 2007.

(60) Provisional application No. 60/796,561, filed on May 2, 2006.

(51) Int. Cl.
*A01N 3/02*　(2006.01)

(52) U.S. Cl.
USPC ........................................................ 504/114

(58) Field of Classification Search
None
See application file for complete search history.

(56) References Cited

U.S. PATENT DOCUMENTS

| 3,089,280 | A | 5/1963 | Klaas |
| 3,157,964 | A | 11/1964 | Ferguson et al. |
| 2004/0186020 | A1 * | 9/2004 | Hinrichs et al. ............... 504/115 |
| 2005/0287257 | A1 | 12/2005 | Martin et al. |

FOREIGN PATENT DOCUMENTS

| CN | 1177443 | * | 4/1998 |
| CN | 1399878 | * | 3/2003 |
| EP | 0398 489 | | 11/1990 |
| JP | 410323121 | * | 12/1998 |
| WO | WO 01/50854 A1 | | 7/2001 |
| WO | WO-0150854 | * | 7/2001 |
| WO | WO 2005/079569 A1 | | 9/2005 |

* cited by examiner

*Primary Examiner* — Alton Pryor
(74) *Attorney, Agent, or Firm* — Merchant & Gould P.C.

(57) ABSTRACT

A composition and method increases storage stability of cut flowers, particularly roses. A liquid composition is applied onto the cut flowers, and then it is converted to a protective polymeric film of a thickness of from about 0.001 to about 0.5 mm.

19 Claims, 1 Drawing Sheet

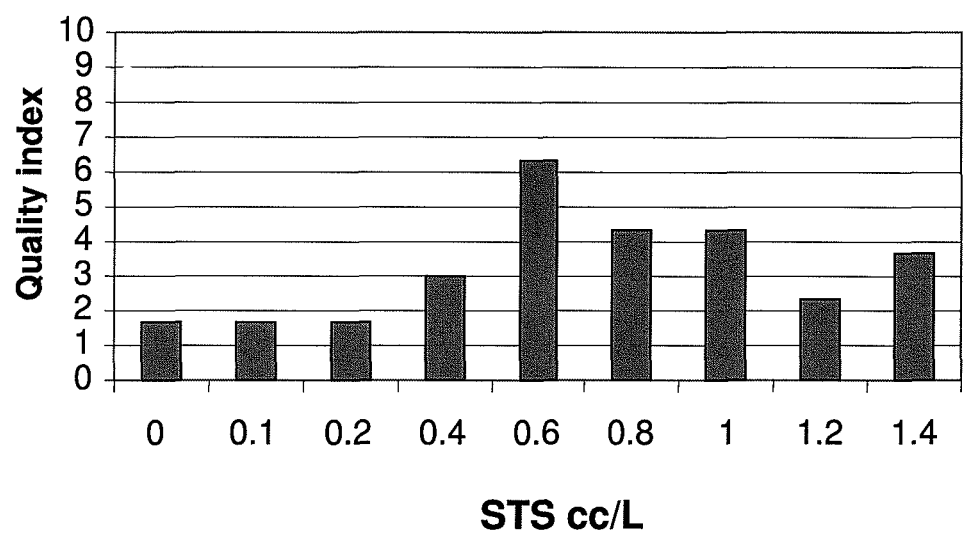

US 8,664,161 B2

METHOD FOR INCREASING LONG-TERM STORAGE OF CUT FLOWERS

This application is a Continuation-in-Part of PCT/IL2007/000529, filed 1 May 2007, which claims benefit of U.S. Ser. No. 60/796,561, filed 2 May 2006, and which applications are incorporated herein by reference. To the extent appropriate, a claim of priority is made to each of the above disclosed applications.

FIELD OF INVENTION

The present invention relates to improving the storage stability of cut flowers or other foliage to be marketed long after harvest time or far from harvest site. More particularly, the present invention relates to a protecting composition, and to a method of increasing the storage time of cut flowers by immersing them in said composition.

BACKGROUND OF THE INVENTION

Ornamental cut flowers and foliage are familiar items of commerce being sold world wide. The majority of these is perishable and has short shelf lives. When the growers are situated a long way from their markets, which is true for most of the trade, it is essential to transport the plant product by air freight. However, the low stability of the cut flowers makes many plant products uneconomical in view the high cost of air freight. The plants suffer from dehydration, infection, and aging due to evolution of endogenous ethylene gas. Various techniques have been described for increasing shelf-life of the cut flowers, often comprising toxic materials, or materials difficult to handle. WO 2005/079569 relates to extending the shelf-life of the cut flowers by contacting the plant with a composition comprising nanocrystalline silver; US 2004/0186020 relates to spraying acrylic latex containing a plant nutrient onto cut plants. The intended use of the considered products, namely items of aesthetics serving as gifts, would be contradicted by the presence of harmful or staining, or otherwise unpleasant, materials. So, it is desirable to avoid, for example, dark silver stains, or a release of toxic substances, or the presence of unpleasant odor associated with acrylic emulsions. It is therefore an object of this invention to provide an efficient and simple method for increasing the storage time of the cut flowers, without conferring to the flowers unpleasant odor.

It is another object of this invention to provide a protecting composition for applying onto cut flowers, enabling long-term storage, without conferring to the flowers unpleasant odor or other annoying properties.

Other objects and advantages of present invention will appear as description proceeds.

SUMMARY OF THE INVENTION

The invention provides a method of increasing storage stability of a cut flower, comprising i) providing an odor-free acrylic emulsion comprising at least one acrylic monomer or oligomer, and a nonionic, non-phytotoxic surfactant; ii) applying said emulsion onto the surface of said flower, thereby forming a layer of said emulsion essentially over the whole surface of said flower; and iii) drying said layer, thereby creating a polymer film having a thickness of from about 0.001 to about 0.5 mm; wherein said emulsion comprises from 0.01 to 6 wt % non-aqueous components, preferably from 0.02 to 1 wt %. Said emulsion layer is consequently converted to a relatively stable film which protects the body of the flower against destructive processes; where "essentially the whole surface" is mentioned, the intention is that the most of the surface is protected which is sufficiently achieved when about 90% or more of the surface is protected, preferably 95% or more. Said step of applying said emulsion comprises dipping or coating or spraying. Said surfactant is preferably a non-phytotoxic surfactant, such as, for example, Tween 20, Agral 90 of Zeneca, or Disponil AFX 4060 Said step of drying results in the formation of a transparent or translucent film, that protects the surface of the plant. Said film is in fact formed during a polymerization process. The resulting polymeric layer should preferably have Tg of less than about 15° C. In a preferred embodiment, the method of the invention comprises a stock composition, from which a working composition for applying onto the flowers is diluted, in a preferred embodiment comprising about 30 wt % acrylate-based components, about 5 wt % surfactants, and a cross-linking monomer in an amount of up to 1 or 2 wt % of said total acrylate-based components, preferably between 0.005 and 1.0 wt %. Said acrylate-based components and said cross-linking monomers may comprise, for example, N-methylol acrylamide, methacrylic acid etc. Additional components may be introduced to contribute to the stability of said flower during the storage, for example biocides, such as silver compounds, triazole, kasugamycin, prochloraz, didecyldimethylammonium chloride, etc. Said stabilizing component may also comprise an ethylene deactivator. Said component may be a post-polymerization additive.

The invention also relates to a cut-flower protecting composition comprising from about 0.01 wt % to about 30 wt % acrylic-based monomer, oligomer, or polymer, and further a surfactant. Acrylic-based materials constitute, in one embodiment of the invention, minimally 0.01 wt % of said protection composition, in other embodiment said acrylic-based materials constitute minimally 0.02 wt %, and in still other embodiment it is minimally 0.5 wt %. After eventual dilution from stock solutions, and before applying onto the flowers, said acrylic-based materials constitute preferably up to 5 wt % of said acrylic-based materials. Cross-linking components may constitute from 0.005 to 2 wt % of said acrylic-based materials, for example from 0.005 to 1%. Said surfactant may constitute up to 8 wt % of said composition, usually up to 6 wt %. In a preferred embodiment of a working protecting composition according to the invention, said acrylic-based materials constitute from about 0.01 to about 5 wt % and said surfactant up to 1 wt %. Said composition may, for example, comprise from 0.1 to 1 wt % nonionic surfactant. In one aspect of the invention, a cut-flower protecting composition comprises, after diluting from a stock composition and before applying onto the flower, from about 0.01 to about 0.5 wt % of acrylic-based materials, more preferably from about 0.01 to about 0.2 wt % acrylic-based material. In a preferred embodiment of the invention, the protected flower is a rose, and said cut-flower protecting composition comprises acrylic-based materials in a concentration of from about 0.01 wt % to about 0.03 wt %.

Said composition forms a layer essentially on the whole surface of a cut-flower and preserves the appearance of said flower without conferring to it an unpleasant odor, which typically accompanies low molecular weight acrylic monomer-based materials such as ethyl or butyl acrylate. This is achieved by the use of high molecular weight non-volatile acrylic monomers. A composition according to the invention may comprise about 30 wt % acrylic-based materials, being used as a stock solution to be diluted before applying onto a cut-flower. Said stock further comprises surfactants in a concentration of up to 5 wt %. The composition of the invention enables long-term storage of cut flowers, while preserving their visual appearance without conferring to them an unpleasant odor. In a preferred embodiment of the invention, a protecting composition is prepared by including acrylic monomers lacking unpleasant odor. Such monomers may comprise, for example, CN152 (Sartomer), or SR506 (Sartomer), or 2-(methacryloyloxy)ethylacetoacetate, but a skilled person, being directed by the present invention, will be able to select other suitable components, preparing, for example, a mixture containing from about 10 to about 30 wt % acrylic-based monomer or oligomer, and a nonionic surfactant. The composition according to the invention further comprises polymerization initiators, biocides, cross-linking agents, or other components.

BRIEF DESCRIPTION OF THE DRAWING

The above and other characteristics and advantages of the invention will be more readily apparent through the following examples, and with reference to the appended drawing, wherein:

FIG. 1 is a graph showing the effect of silver thiosulfate concentration in an acrylic emulsion on the quality of cut roses treated according to one embodiment of the invention, after one month of storage, as described in Example 4.

DETAILED DESCRIPTION OF PREFERRED EMBODIMENTS

It has now been found that dipping a cut flower in an acrylic emulsion containing up to 5 wt % of acrylic-based material selected so as not to confer any unpleasant odor to the product, together with suitable surfactants, substantially increases the storage time of the flower product. It turns out that a composition according to the invention solves the above mentioned problems associated with long term storage and long transport, extending the shelf life of the plants by a number of weeks, while keeping the cut flowers attractive, and while avoiding any unpleasant odor due to the used materials.

The invention provides an acrylic emulsion for applying onto the plants by a dipping, coating or spraying process. On drying, a thin film of a few microns thickness is formed, acting as a barrier which slows the rate of water loss. The film further protects the plant surface, and inhibits the development of the various plant pests and diseases. In a preferred embodiment of the invention, specific additives enhancing said protective effect are added to the acrylic emulsion. Such additives may inhibit microbial growth or deactivate ethylene.

Applying said acrylic emulsion on the surface of a plant followed by drying, leads to the formation of a polymeric layer. The polymer preferably has some of the following properties, combined according to specific applications and needs.

a) The polymer is prepared as a water-based acrylic emulsion containing about 30% solids, followed by desired dilutions. On drying, these solids coalesce or react to form a transparent and preferably glossy film on the leaves of the plant.
b) The surface tension of the emulsion is below about 30 dyne/cm to ensure good wetting of the leaves and adhesion to the leaves.
c) The surface energy of the cured polymer film is preferably similar to that of the plant leaves to ensure good adhesion.
d) The polymer film is preferably biodegradable after the plant is discarded.
e) The film, formed on the surface of the plant, is flexible under temperatures preferably corresponding to European or US winter conditions, and has limited permeability for gases and water.
f) The materials contacting the leaves are preferably non-phytotoxic and do not cause damage to the plant.
g) Specifically, a non-phytotoxic surfactant is selected for the emulsion preparation. In general, non ionic surfactants are preferred.
h) No harmful materials are emitted from the cured film.

The copolymer emulsions for use according to the invention meet as many as possible of the above requirements simultaneously. Some commercial emulsions are phytotoxic due to the used surfactants. The invention avoids the use of harmful surfactants, employing surfactants used in agricultural applications, such as Tween 20 (see Example 1). Furthermore, relating to the mechanical properties of the film which protects the plant surface in a method of this invention, it was found that the glass transition temperature (Tg) of the copolymer is an important parameter. A suitable Tg value is, for example, around 20° C.

For reasons of mechanical strength, and to prevent polymers from being sticky, in a preferred embodiment of the invention, the polymer that is formed is consequently cross-linked. The levels of cross-linking monomers are up to 2% by weight of the total monomers, preferably between 0.005 and 1.0 wt %. Each cross-linker requires its specific reagent for the cross-linking reaction. These reactions are usually condensation reactions and release a small volatile molecule. Those reactions that release toxic molecules such as formaldehyde will be avoided in favor of safer by-products.

In a preferred method of the invention, the storage stability of the cut flowers is enhanced by including additional agents contributing to the flower stability, for example, antimicrobial or antiaging materials, such an silver thiosulfate which may be added to cut flowers as a pulsing solution, or as part of the film. Biocides may be added to emulsions that are applied according to the invention, such as triazole or kasugamycin or prochloraz or didecyldimethylammonium chloride. Specifically, in a preferred embodiment of the invention, spores and fungi which commonly attack plant tissue during storage are eliminated. Specific target species may include, for example, *Botrytis, Alterneria*, etc.

The invention, thus, provides a composition and method enabling a long-term storage of cut flowers, while not only preserving their visual appearance, but while also avoiding any unpleasant phenomena, such as staining contacted surfaces. Importantly, any unpleasant odors are avoided, such as odors caused by low molecular weight acrylic monomers. Furthermore, the presence of any plant nutrient is not needed. In a method according to the invention, acrylate monomers or oligomers are used that do not exhibit unpleasant odor, examples being, CN152 (Sartomer), SR506 (Sartomer), 2-(methacryloyloxy) ethylacetoacetate; but the invention is not limited to these examples. The stock composition may comprise, for example, about 30% acrylate monomers and/or oligomers as copolymers; the working emulsion, obtained by diluting said stock may comprise a concentration of from about 0.005 to 5.0%. Said stock composition contains surfactants, preferably nonionic, and an initiator is comprised when the polymerization is desired. The surfactants may have a concentration of from about 1 to about 8 wt %. A typical stock solution contains usually from 27 to 31 wt % acrylate monomers or oligomers as copolymers, and from 3.5 to 6 wt % surfactants.

The invention will be further described and illustrated by the following examples.

EXAMPLES

General

During developing the copolymer emulsion, the synthesis in a reactor produced about liter emulsion by the procedure described below. Emulsion was characterized by the following tests: checking spreading on leaves, measuring glass transition temperature (Tg) by differential scanning calorimeter (DSC), and measuring surface energy using standard solutions for wetting.

The cut flowers were dipped either in water of in the acrylic emulsion, and it was found that the flowers treated according to the invention had a storage life longer by at least four weeks.

Example 1

Phytotoxicity Test of Surfactants on Cut Rose Flowers

Cut flowers of Roses of the Akito variety, an intermediate type of rose, were harvested in a commercial roses green house in Menucha village. The flowers were dipped in different surfactants in several concentration of the surfactant. The highest surfactant concentration was 2% by weight and the lowest concentration was 0.005%. The dilution was with reverse osmosis water.

At each concentration we dipped the flowers in the solution for 20 seconds. Each treatment included 10 flowers. After the dip process we held the flowers with the heads up side down for 15 minutes so that excess solution could drain off. The dry flowers were kept in allocated vases for quality and shelf life test. The quality and appearance of the flowers were checked every day.

The results in the following Table 1 indicate the quality of the flowers after one week in the test room. Positive implies a good appearance, negative implies damage to the flower.

TABLE 1

| Surfactant | Surfactant Concentration, % | | | | | | | | |
|---|---|---|---|---|---|---|---|---|---|
| Name | 2 | 1 | 0.5 | 0.20 | 0.10 | 0.05 | 0.02 | 0.01 | 0.005 |
| AGRAL 90 | NEG | NEG | NEG | POS | POS | POS | POS | POS | POS |
| TWEEN 20 | NEG | NEG | NEG | NEG | NEG | NEG | NEG | POS | POS |
| Disponil AFX 4060 | NEG | POS | POS | POS | POS | POS | POS | POS | POS |
| Disponil AFX 5060 | NEG | NEG | NEG | POS | POS | POS | POS | POS | POS |

NEG means the test failed.
POS means the test succeeded

Example 2

Procedure:
Pre-Emulsion Preparation:

7.5 g sodium dodecylbenzene sulfonate was completely dissolved in 484g deionized water by mixing with a magnetic stirrer. Then 54 g Disponil AFX 4060 were added to form a transparent viscous surfactant solution. In a 0.5 liter beaker were placed all of the monomers. This monomer solution was poured into the surfactant solution and mixed to give a pre-emulsion. The pre-emulsion was kept for 20 hours in a refrigerator.

Polymerization:

To the pre-emulsion were added 0.6 g ammonium per sulfate and it was stirred with a magnetic stirrer for 0.5 h. 200 ml of water were added to the reactor and the mechanical stirrer was set at 300 rpm. Then 200ml of pre-emulsion were added. Nitrogen gas was purged through the mixture for 30 minutes. Some foam may be formed at this stage. The reactor was then placed in the oil bath and heated to 84° C. and then the remainder of the pre-emulsion was added to the reactor during two hours and 10 minutes using a peristaltic pump. To complete the polymerization, 60 mg of ammonium per sulfate were added and the temperature was raised to 95-97° C. for an additional hour. The heating was shut off and the contents of the reactor were cooled slowly with continuous stirring with the reactor remaining in the oil bath. The emulsion polymer product, a synthetic latex, was removed from the reactor and filtered through a synthetic non-woven cloth. No coagulation product was observed. The pH of the emulsion was 2.7 The pH was raised to 8.0 by carefully adding about twenty two drops of 25% ammonium hydroxide. This was monitored using a pH electrode. The final yield was 1007.4 g

Example 3

Emulsion composition comprised the following materials was prepared as stated in example 2:
Monomers:
45 g CN152 (Sartomer), low viscosity monoacrylate monomer,
82.5 g SR506 (Sartomer), isobornyl monoacrylate,
22.5 g 2-(methacryloyloxy)ethylacetoacetate (AAEM),
Surfactants
3.75 g sodium dodecylbenzene sulfonate, 80%,
18.0 g Shatah 90
Initiator
0.33 g ammonium persulfate;
Water, 350 g
30% ammonia, several drops, to adjust the pH to 8.
Analyses:
$T_g$ by DSC=17° C., Total solids=32.8%

The emulsion was used for applying onto flowers, which then exhibited prolonged storage stability, enabling their long-term storage of minimally 4 weeks.

Example 4

The effect of silver thiosulfate (STS) solution in the acrylic emulsion on the quality of cut Rose Flowers (Akito and Red One varieties, an intermediate types of roses, harvested in a commercial roses green house in Menucha village, Israel) was examined after dipping and storing for one month. The flowers were dipped in several emulsions that included several concentration of STS (diluted from 8 g/l by taking from 0.1 to 1.4 ml per liter), ranging from 0.8 to 11.2 ppm. A bunch of roses, flowers and leaves, was dipped in the solution at each concentration for 2 seconds three times. Each treatment included 10 flowers. After the dip process, the flowers were put on a net for 10 minutes, so that an excess solution could drain off. The flowers were kept in an impregnation box at 2° C. for one month, and then they were allocated in vases for quality and shelf life assessments. The quality and appearance of the flowers were checked every day (FIG. 1). It can be seen that the silver salt in a concentration of several ppm improves the quality of the stored roses.

Example 5

The effect of an acrylic emulsion according to the invention (denoted as D60) on the quality of cut roses (the roses of the same type as in Example 4) after dipping and storing for one month was checked. The flowers were dipped in a solution that included:
1. 100-200 ppm of the acrylic polymer (diluted from the emulsion of Example 3);
2. 3 ppm of silver thiosulfate; and
3. 0.02% Prochloraz (diluted from 45%).

The cut flowers were dipped (flowers and leaves) in D60 solution for 2 seconds three times. After the dipping process, the flowers were drained for 10 minutes to get rid of an excess solution. These flowers were kept in a cardboard box in at 2° C. for one month. After one month the flowers were allocated in vases for quality and shelf life assessment. The quality and appearance of the flowers were checked every day. The treated roses were keeping their fresh appearance even after one month, whereas comparison samples of non-treated roses, dipped only in water but kept under the same storage conditions, showed symptoms of advanced withering. The roses in the comparison samples, both white and red samples, exhibited color and shape changes; their petals turned partially brown, and deformed. The treated roses showed no such withering signs in any of the colors.

While the invention has been described using some specific examples, many modifications and variations are possible. It is therefore understood that the invention is not intended to be limited in any way, other than by the scope of the appended claims.

The invention claimed is:

1. A cut rose protecting composition for increasing storage stability of a cut rose after one week to at least four weeks while preserving visual appearance without giving to the cut rose an unpleasant odor, the composition comprising from about 0.01 wt % to about 30 wt % at least one acrylic-based components selected from monomer, oligomer, or polymer lacking an unpleasant odor, a cross-linking monomer in an amount of from 0.005% to 2% of said acrylic-based components, and about 0.01 wt % to about 6 wt % surfactant comprising the nonionic surfactant ethoxylated nonylphenol.

2. A cut rose protecting composition according to claim 1, comprising from about 0.01 to about 5 wt % acrylic-based materials and up to 1 wt % of the nonionic surfactant.

3. A cut rose protecting composition according to claim 1, comprising from about 0.01 to 0.5 wt % acrylic-based material.

4. A cut rose protecting composition according to claim 1, comprising from about 0.01 to 0.2 wt % acrylic-based material.

5. A cut rose protecting composition according to claim 1, wherein said flower is a rose, and wherein said acrylic-based material has a concentration of from about 0.01 wt % to about 0.03 wt %.

6. A composition according to claim 1, forming after drying, a layer having a thickness of from about 0.001 to about 0.5 mm, essentially on the whole surface of said cut rose, the layer being a transparent or translucent film.

7. A composition according to claim 1, comprising about 30 wt % acrylic-based materials, being a stock solution to be diluted before applying onto a cut-flower.

8. A composition according to claim 1, comprising an acrylate-based component selected from oligomers.

9. A composition according to claim 1, further comprising biocides.

10. A composition according to claim 9, wherein said biocide is prochloraz.

11. A method of increasing storage stability of a cut rose by employing the protecting composition of claim 1, comprising:
   i) providing an acrylic emulsion comprising the at least one acrylic monomer or oligomer, and the nonionic surfactant;
   ii) applying said emulsion onto the surface of said flower, thereby forming a layer of said emulsion essentially over the whole surface of said flower; and
   iii) drying said layer, thereby creating a polymer film having a thickness of from about 0.001 to about 0.5 mm;
   wherein said emulsion comprises from 0.01 wt % to 6 wt % non-aqueous components.

12. A method according to claim 11, wherein said applying said emulsion comprises dipping or coating or spraying.

13. A method according to claim 11, wherein said drying results in the formation of a transparent or translucent film.

14. A method according to claim 13, wherein said film is a polymeric film.

15. A method according to claim 11, wherein said emulsion comprises an additional component that contributes to the stability of said flower during the storage.

16. A method according to claim 15, wherein said additional component is a biocide.

17. A method according to claim 16, wherein said biocide is selected from the group consisting of silver compounds, triazole, kasugamycin, prochloraz, and didecyldimethylammonium chloride.

18. A method according to claim 15, wherein said additional component is an ethylene deactivator.

19. A method according to claim 15, wherein said additional component is a post-polymerization additive.

* * * * *